United States Patent [19]

Solazzi

[11] Patent Number: 4,643,033
[45] Date of Patent: Feb. 17, 1987

[54] SAMPLE CUP FOR USE IN X-RAY SPECTROSCOPY

[75] Inventor: Monte J. Solazzi, Eastchester, N.Y.

[73] Assignee: Chemplex Industries, Inc., Tuckahoe, N.Y.

[21] Appl. No.: 778,079

[22] Filed: Sep. 20, 1985

[51] Int. Cl.⁴ .................................................. G01N 1/10
[52] U.S. Cl. ................... 73/864.91; 356/246; 378/208
[58] Field of Search ............. 73/864.91; 356/246; 422/102; 378/204, 47, 208, 79; 206/628; 250/428; D24/2, 9; 220/356, 351, 306

[56] References Cited

U.S. PATENT DOCUMENTS

| D. 238,693 | 2/1976 | Solazzi | D24/2 |
| 3,218,459 | 11/1965 | Bens | 378/47 |
| 4,037,109 | 7/1977 | Hosokawa et al. | 356/246 |
| 4,115,689 | 9/1978 | Won | 378/47 |
| 4,409,854 | 10/1983 | Solazzi | 356/246 |
| 4,448,311 | 5/1984 | Houser | 378/208 |
| 4,575,869 | 3/1986 | Torrisi et al. | 356/246 |

FOREIGN PATENT DOCUMENTS 1222425  8/1966  Fed. Rep. of Germany ...... 220/306

Primary Examiner—Jerry W. Myracle
Assistant Examiner—Robert R. Raevis
Attorney, Agent, or Firm—Arthur L. Plevy

[57] ABSTRACT

There is disclosed a sample cup for retaining a specimen to be subjected to spectrochemical analysis. The sample cup comprises a cell section which is a cup-shaped member having a closed bottom and an opened top, the opened top being defined by a cell neck having a tapered outer wall. The tapered outer wall of the cell neck is adapted to receive an annular collar having an integrally molded thin plastic film for covering the opened top, thereby sealing the specimen prior to the spectrochemical analysis.

19 Claims, 3 Drawing Figures

SAMPLE CUP FOR USE IN X-RAY SPECTROSCOPY

BACKGROUND OF THE INVENTION

This invention relates to a sample cup for use in holding specimens for spectrochemical analysis and, more particularly, to a sample cup including an annular collar having an integrally molded thin film therein.

Sample cups for spectrochemical analysis are used in the prior art to hold or contain liquid, solids, and powdered specimens under normal atmospheric pressures, gas pressures, or in vacuum for analysis such as energy and wave length dispersive techniques and optical emission methods. Such cups, as indicated, are in widespread use.

Essentially, the sample cup consists of three components, a cup-shaped cell having a closed bottom and an opened top, an annular collar, and a snap-on ring. Typical prior art cups are shown in U.S. Pat. No. Des. 238,693 entitled "Cell for X-Ray Spectroscopy or Similar Article" issued on Feb. 3, 1976 to Monte J. Solazzi and U.S. Pat. No. 4,409,854 entitled "Sample Cup with Venting Means for Use in X-Ray Spectroscopy" issued on Oct. 18, 1983 to Michael C. Solazzi, and assigned to the assignee herein.

The collar and the snap-on ring serve to secure a sheet of plastic material such as MYLAR, the trademark for a polyester film sold by E. I. duPont de Nemours and Co., to cover the opened top of the cell when the hollow of the cell is filled with a specimen such as a liquid, solid, or powdered material to be analyzed. Such cells are available from many sources including the assignee Chemplex Industries, Inc., of 140 Marbledale Road, Eastchester, N.Y. 10707.

For spectrochemical analytical investigation of specimens characterized with high abrogation properties in air, the entire assembled sample cup with the plastic sheet covering the top may be then placed within a vacuum or an inert gas environment. Under conditions where pressure equalization is not implemented, the plastic sheet will distend or bow outwardly due to the vacuum or lower pressure. This then places the surface of the sheet closer to the excitation source which may be an X-ray tube or other device. The surface of the sheet of plastic is commonly defined as the sample plane. A variation in the distance from the sample plane to the source of excitation operates to alter the intensity of the characteristic radiation of the specimen and also the intensity of radiation impinging upon the sample from the excitation source. The variations result in erroneous quantitative data and hence cannot be tolerated. As indicated, for applications in a vacuum environment, the thin plastic film distorts or bows out (convex), which decreases the distance from the sample to the excitation source. For applications in a gaseous environment (positive pressure), the thin plastic film tends to be drawn into the hollow of the cell or provides a concave surface. This effect increases the distance between the sample plane and the excitation source. Based upon the distortions of the thin film, the results or analytical data obtained can be of a higher or lower value than would be expected without distortion.

Moreover, it has been found when using the thin plastic sheet that problems arise with tautness of the sheet and, further, with wrinkles being formed in the sheet during operation. It has also been found that when attempting to fasten the thin film material to the sample cup, there is a tendency for the side of the opened top portion of the cup to rip the thin sheet material. Thus the prior art uses of thin plastic sheets are not convenient ways of providing a closure for the sample cup.

It is therefore an object of the present invention to provide an improved sample cup including an annular collar which has an integrally formed thin plastic film therein which enables an operator to conveniently fill and assemble the sample cup therefore eliminating the need for the separate attachment of a thin-film sample support material and the corresponding collars to position it correctly.

DESCRIPTION OF THE PREFERRED EMBODIMENT

A sample cup for retaining a specimen to be subjected to spectrochemical analysis constitutes a cell section which is a cup-shaped member having a closed bottom and an opened top, said opened top being defined by a cell neck having a tapered outer wall, the tapered outer wall of said cell neck being adapted to receive an annular collar having an integrally molded thin plastic film for covering said opened top, thereby sealing the specimen prior to the spectrochemical analysis.

DETAILED DESCRIPTION OF THE INVENTION

Figure 1:
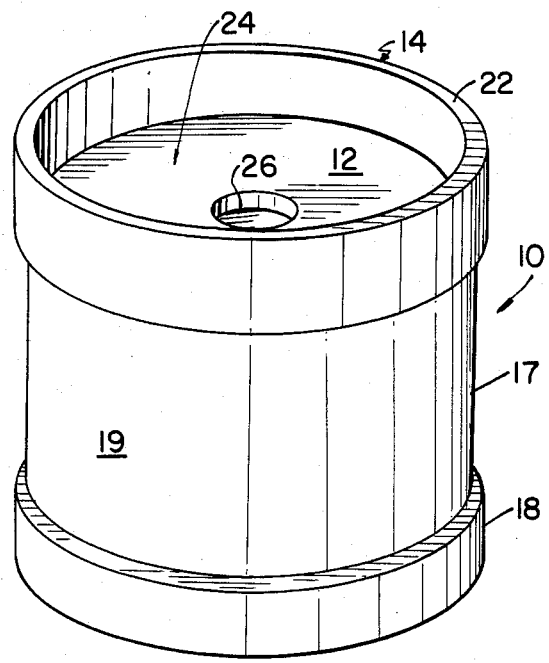
FIG. 1 is a perspective plan view of a sample cup according to this invention.

Referring to FIG. 1, there is shown a sample cup 10. The sample cup 10 is shown with the bottom surface 12 of the closed bottom 14 facing upward. As will be explained, the cup has an opened top 16 and is generally cylindrical in shape. The sample cup consists essentially of two components. There is a main cell component 17, which is essentially a cup-like member having an opened top 16 and a closed bottom 14 and a cylindrical wall 19. There is shown an annular member or annular collar 18, which is provided with an integrally molded thin plastic film for closing the opened top. The integrally molded thin film of annular collar 18 and the cylindrical wall 19 of the main cell component define a hollow 20 within the confines of the cell 17. The closed bottom 14 of the cell 17 can have an extending peripheral flange 22, which encircles the bottom surface 12 of the closed bottom 14. This provides for an overflow reservoir 24. It should be noted that although an overflow reservoir is shown, the sample cup of the present invention is not required to have the same. Additionally, there is shown vent hole provision 26 in bottom surface 12 of closed bottom 14. Again the cell can be provided with a vent hole, but this is not a feature of the present invention.

Figure 2:
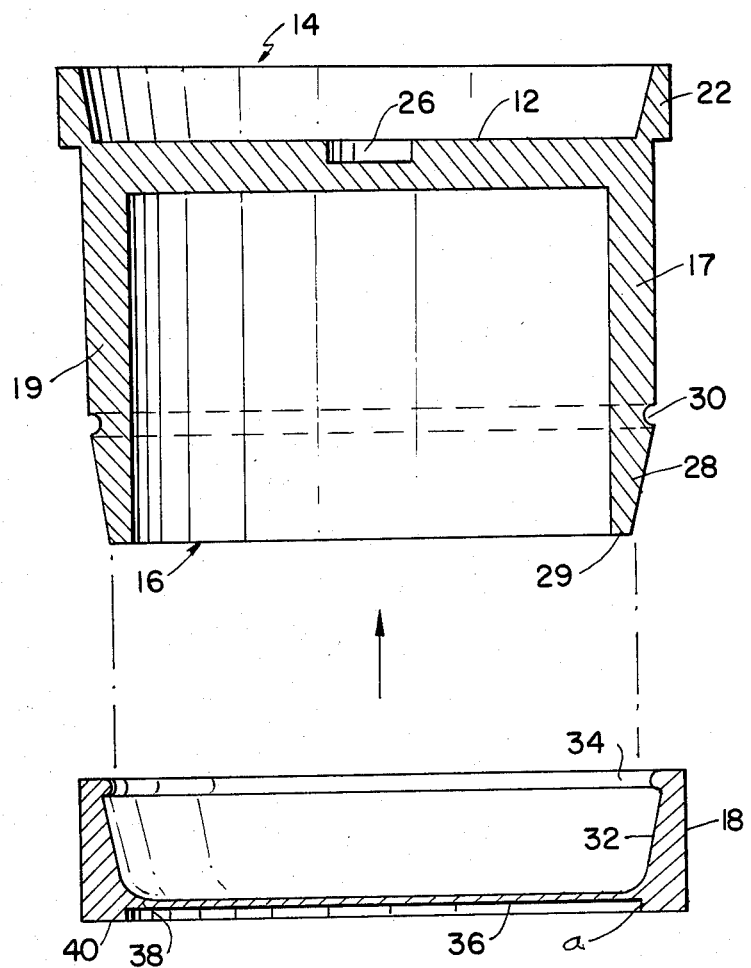
FIG. 2 is an assembly view in cross-section of the components constituting the sample cup.

Referring to FIG. 2, there is shown a cross-sectional view of the sample cup 10 clearly depicting the cell 17 and the annular collar 18. Referring to FIG. 2, the cell 17 is generally cylindrical in structure and is fabricated from a suitable plastic such as polypropylene. Polypropylene and other plastics as well offer rigidity and have resistance to chemical attack. Thus these plastics are particularly useful in providing sample cup structures.

The cell 17 has a tapered cell neck portion 28 about the open top 16 thereof and is defined by a top edge 29 and a circumferential groove 30. The cell neck 28, edge 29, and groove 30 are adapted to coact with and retain the annular collar member 18 in position.

As further can be seen from FIG. 2, the annular collar member 18 has interior tapered sides 32 which correspond to the taper of cell neck 28 of cell 17. There is also an extending circular projection or flange 34 which fits into groove 30 to thereby hold the annular collar 18 in place on cell 17. As previously stated, annular collar 18 is provided with an integrally molded thin film 36. Thin film 36 is unitized and seamless in construction to avert potential leaks resulting in loss of specimen and damage to the spectrochemical instrumentation. Thin film 36 is provided at its periphery with a tapered shoulder portion 38, which has a width extending inwardly from tapered sides 32 of annular collar 18 a distance which is approximately equal to the thickness of the edge 29 of cell neck 28 of cell 17. Tapered shoulder portion 38 provides a secondary seal against the potential possibility of leakage, especially important if liquids are to be subject to spectrochemical analysis in vacuum and the entire system is not vented-that is, under positive pressure relevant to its external vacuum environment in the spectrometer. About its center thin film 36 is approximately 0.00025 inches to 0.005 inches in gauge. Collar 18 is also provided with annular flange 40, which results in thin film 36 being recessed, as shown in FIG. 2 as within annular collar 18 to prevent contamination or breakage.

Thin film 36 and annular collar 18 are fabricated from unrecycled polyethylene and are free of metallic properties by processes such as injection molding. In this regard, tapered shoulder portion 38 provides an additional advantage in simplifying the injection molding of thin film 36 since sharp corners are avoided. Polyethylene is one of a number of thermoplastic materials that can be utilized in this application because of its excellent mass attenuation properties encompassing the 1 to 12 Angstrom analyte wavelength range in addition to resistance to chemical (sample) attack, temperature softening, and degradation from excitation energy sources. It also exhibits excellent tensile strength for adequate sample retention and, most importantly, provides an excellent "general purpose" thin-film sample support applicable to both short (energetic) and long (soft) wavelength studies.

Figure 3:
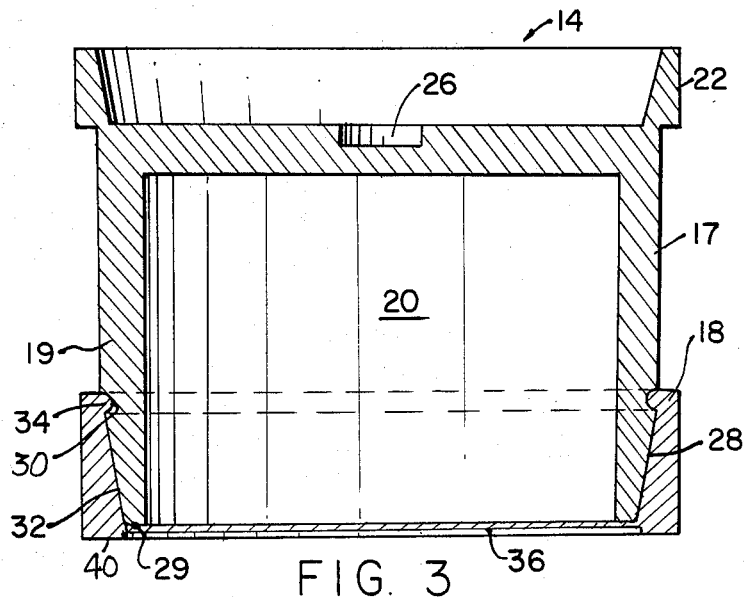
FIG. 3 is a cross-sectional view of the assembled sample cup.

Referring to FIG. 3, there is shown a cross-sectional view of the sample cup 10 encompassing both main cell 17 and annular collar 18. In order to use the cup 10, a sample of material is introduced into the hollow 20 of the cell 17. To do this, the cell is inverted from the position shown in FIGS. 2 and 3, and thus the opened top 16 of cell 17 is facing upward. The sample as introduced fills the hollow 20 to the edge 29 of the cell 17. The annular collar 18 with the integrally molded thin film 36 is then placed over the opening 16 such that the edge 29 of the cell neck 28 is in contact with the tapered shoulder portion of the thin film 36. Upon further downward pressure, edge 29 of cell 17 exerts pressure on thin film 36 and pushes the film both outwardly and upwardly towards the upper surface of the annular collar 18 defined by the upper surface of the flange 40 from the distance "a" approximately equivalent to the original recessed depth defined by flange 40 to a depth "b" of less than about 0.001 inches, so as to prevent the actual stretched film 36 from making contact with a table or counter surface and becoming contaminated or punctured. During this assembly process, thin film 36 is stretched uniformly and circumferentially and hence maintains its tautness, providing a wrinkle-free sample surface. In this regard, tapered shoulder portion 38 serves as a secondary gasket seal against the cell neck edge 29 for an extra sealant especially for vacuum or inert gas spectrochemical analysis. Annular collar 18 is pushed downwardly such that circular projection 34 is captured by circumferential groove 30, thereby retaining annular collar 18 on cell 17.

Naturally, the invention is not limited solely to the embodiment described above but may be modified within the scope of the following claims.

What is claimed is:

1. A sample cup for retaining a specimen to be subject to spectrochemical analysis, comprising:
   a cup-shaped member having a closd bottom surface and an opened top and an annular collar for encircling said opened top, said annular collar having an integrally molded thin film for closing said opened top and including sealing means to seal said specimen within said cup-shaped member during spectrochemical analysis, said annular collar being thick with respect to said integrally molded thin film and said integrally molded thin film being sufficiently thin to enable said specimen contained within said cup-shaped member to be subjected to radiation during said spectrochemical analysis without significantly altering the characteristic radiation of said specimen or the intensity of said radiation impinging upon said specimen within said cup-shaped member.

2. A sample cup according to claim 1 wherein the bottom of said closed bottom surface of said cup-shaped member further includes a continuous extending peripheral flange located about the outer edge of said closed bottom surface.

3. The sample cup according to claim 1 wherein the bottom of said closed bottom surface of said cup-shaped member further includes means for venting said sample cup.

4. The sample cup according to claim 1 wherein said cup-shaped member is provided with a tapered neck portion having an edge portion at said opened top and a circumferential groove located on the outer surface of said cup-shaped member spaced away from said edge portion.

5. The sample cup according to claim 4 wherein said sealing means comprises an inwardly directed peripheral flange, said inwardly directed peripheral flange for coacting with said circumferential groove on said outer surface of said cup-shaped member to seal said annular collar to said cup-shaped member.

6. The sample cup according to claim 1 wherein said annular collar includes a first end and a second end, said first end of said annular collar being adapted to be attached to said cup-shaped member and said second end of said annular collar including said integrally molded thin film, said integrally molded thin film being recessed from said second end of said annular collar.

7. The sample cup according to claim 1 wherein said annular collar and integrally molded thin film are fabricated from polyethylene.

8. The sample cup according to claim 1 wherein said integrally molded thiin film is of a gauge of 0.00025 to 0.0005 inches.

9. In a method for subjecting a sample to spectrochemical analysis wherein said sample is retained within a sample cup having a closed bottom surface and an opened top where said top is covered by a separate thin plastic film after the specimen is introduced into said cup with said thin plastic film undesirably distorting and providing a concave or convex surface during said analysis, the improvement comprising:

placing an annular collar including an integrally molded thin film about said opened top, said annular collar further comprising sealing means to seal said specimen within said sample cup during said spectrochemical analysis to thereby eliminate the need for said separate thin plastic film and wherein said integrally molded thin film is provided with a peripherally positioned tapered shoulder portion abutting the interior wall of said annular collar, said integrally molded thin film being sufficiently thin whereby said sample may be subjected to radiation during said spectrochemical analysis without significantly altering the characteristic radiation of said sample or the intensity of said radiation impinging upon said sample.

10. The method according to claim 9 wherein the bottom of said closed bottom surface of said sample cup further includes a continuous extending peripheral flange located about the outer edge of said closed bottom surface.

11. The method according to claim 9 wherein the bottom of said closed bottom surface of said sample cup further includes means for venting said sample cup.

12. The method according to claim 9 wherein said sample cup is provided with a tapered neck portion having an edge portion at said opened top and a circumferential groove located on the outer surface of said sample cup spaced away from said edge.

13. The method according to claim 12 wherein said annular collar further comprises an inwardly directed peripheral flange, said inwardly directed peripheral flange being adapted to coact with said circumferential groove on said outer surface of said sample cup to secure said annular collar to said sample cup.

14. The method according to claim 9 wherein said sample cup is provided with a tapered neck portion having an edge portion of a predetermined thickness at said opened top, and wherein said peripherally positioned tapered shoulder portion has an arc shaped configuration, the length of said arc substantially corresponding to said predetermined thickness of said edge portion of said tapered neck portion of said sample cup.

15. The method according to claim 9 wherein said annular collar includes a first end and a second end, said first end of said annular collar being adapted to be attached to said sample cup and said second end of said cup shaped member including said integrally molded thin film, said integrally molded thin film being recessed from said second end of said annular collar.

16. The method according to claim 9 wherein said annular collar and integrally molded thin film are fabricated from polyethylene.

17. The method according to claim 9 wherein said integrally molded thin film is of a gauge of 0.00025 to 0.0005 inches.

18. A sample cup for retaining a specimen to be subjected to spectrochemical analysis, comprising:

a cup-shaped member having a closed bottom surface and an opened top and an annular collar adapted to encircle said opened top, said annular collar having an integrally molded thin film adapted to close said opened top and including sealing means to seal said specimen within said cup-shaped member during spectrochemical analysis, said integrally molded thin film being sufficiently thin whereby said specimen contained within said cup-shaped member may be subjected to radiation during said spectrochemical analysis without significantly altering the characteristic radiation of said specimen or the intensity of said radiation impinging upon said specimen within said cup-shaped member, said integrally molded thin film being provided with a peripherally positioned tapered shoulder portion abutting an interior wall of said annular collar.

19. The sample cup according to claim 18 wherein said cup-shaped member is provided with a tapered neck portion having an edge portion of a predetermined thickness at said opened top, and wherein said peripherally positioned tapered shoulder portion has an arc shaped configuration, the length of said arc substantially corresponding to said predetermined thickness of said edge portion of said tapered neck portion of said cup-shaped member.

* * * * *